United States Patent [19]

Warshaw

[11] Patent Number: 5,240,945
[45] Date of Patent: Aug. 31, 1993

[54] METHOD AND COMPOSITIONS FOR TREATING ACNE

[76] Inventor: Thelma G. Warshaw, 519 E. Broad St., Westfield, N.J. 07090

[21] Appl. No.: 836,414

[22] Filed: Feb. 18, 1992

[51] Int. Cl.⁵ .......................... A61K 7/48; A61K 9/10; A61K 31/44

[52] U.S. Cl. .................... 514/356; 514/844; 514/859; 514/937; 514/938; 514/944

[58] Field of Search .................. 514/844, 859, 356

[56] References Cited

U.S. PATENT DOCUMENTS 4,123,433  10/1978  Sherlock ........................... 514/859
4,127,662  11/1978  Sherlock ........................... 514/859

OTHER PUBLICATIONS

Chem. Abstracts, 1990, vol. 112(18): 164983e (Apr. 30, 1990) (Abstract of Great Britain 2,210,789, Jun. 21, 1989), Morrison.

Chem. Abstracts, 1983, vol. 97(10): 789246 (Europat 52705 Jun. 2, 1982), Bernstein May 21, 1979.

Chem. Abstracts, 1980, vol. 90(21): 168465n, Sherlock Oct. 10, 1977.

Chem. Abstracts, 1978, vol. 87(15): 117787z, Sherlock(I).

The Merck Index, 1976, 9th edition, #5966, p. 795, published by Merck & Co. Inc.

Chem. Abstracts, 1991, vol. 115(22): 239792q Leung.

*Primary Examiner*—Dale R. Ore
*Attorney, Agent, or Firm*—Mathews, Woodbridge & Collins

[57] ABSTRACT

Topical application of a lower alkyl nicotinate to the locus of a conglobate or cystic acne papule can effect rapid improvement in the lesion and often reduce the pain associated with such lesions. Typical embodiments include topical formulations of methyl nicotinate in a cream base.

5 Claims, No Drawings

METHOD AND COMPOSITIONS FOR TREATING ACNE

DETAILED DESCRIPTION

The present invention pertains to a method of treating acne and to compositions useful in the practice of that method.

While presently not curable, acne can be successfully treated in many cases. Therapies currently in use or suggested, include the application of compositions containing such agents as benzoyl peroxide, sulfur, retinoic acid (including derivatives thereof) and salicylic acid. Many of these produce redness, peeling and desquamation of the treated skin. In addition, there is some evidence that benzoyl peroxide may have antibacterial action against *Propionibacterium acnes* (*P.acnes*), one of the principal microorganisms associated with the condition. My U.S. Pat. No. 4,450,175 describes the use of nitrates and nitrites in the treatment of acne.

The present invention is based on the discovery that the topical application of a lower alkyl nicotinate to the locus of a conglobate or cystic acne papule can effect rapid improvement in the lesion and often reduce the pain associated with such lesions. Included within the term lower alkyl nicotinate are the straight and branched chain alkyl esters of nicotinic acid, as for example methyl nicotinate, ethyl nicotinate, propyl nicotinate, isopropyl nicotinate, n-butyl nicotinate, t-butyl nicotinate, pentyl nicotinate, neo-pentyl nicotinate, hexyl nicotinate, and the like nicotinates. These compounds in general can be represented by the formula:

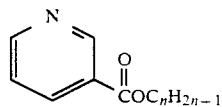

in which n has a value of from 1 to 6.

Without wishing to be bound by any theory of action, it appears the effectiveness of the nicotinates involves assisting the body's own defense against infection. *P.acnes* is a facultative anaerobic bacterium commonly found in acne papules and the presence of an anaerobic infection in otherwise healthy patients may be traceable to a temporary inadequacy in vascular supply in the rapidly enlarging pilosebaceous organ in which the acne process occurs. This impairment of vascular circulation not only may produce inadequate oxidation, permitting facultative anaerobes to thrive, but also reduce the effectiveness of *P.acnes* antibodies, titers of which generally parallel the clinical severity of the acne. Moreover the increase in circulation to the lesion will produce a reduction in the pain associated with cystic lesions.

Ordinarily the compositions can contain from about 0.5 to about 2% by weight of the nicotinate, preferably from about 0.5 to 1%. The remainder of the composition will comprise carriers suitable for cream, ointment, or gel formulations well known in this field; see e.g., U.S. Pat. No. 4,318,907. Systemic vasodilating activity is not required but the formulation should enhance local activity. Although ointment bases such as lanolin, higher alkyl alcohols, petrolatum and similar lipophilic materials can be used, heavy or greasy formulations should be avoided. Lotions, creams, and gels are particularly preferred. Typical formulations are as follows:

| Composition I | |
| --- | --- |
| Methyl nicotinate | 0.5 g |
| Cetaphil Cream | 99.5 g |

The above ingredients are thoroughly blended producing a homogeneous cream. Cetaphil cream is a commercial blend of water, cetyl alcohol, propylene glycol, sodium lauryl sulfate, and stearyl alcohol, together with preservatives (methyl paraben, propyl paraben, and butyl paraben).

| Composition II | |
| --- | --- |
| Methyl nicotinate | 1.1 g |
| Lanolin | 25.0 g |
| White petrolatum | 73.9 g |

The above ingredients are thoroughly blended producing a homogeneous ointment.

Composition II

A lotion formulation is prepared from 0.5% methyl nicotinate and 99.5% of a commercial lotion base of water, cetyl alcohol, propylene glycol, sodium lauryl sulfate, and stearyl alcohol, together with preservatives (methyl paraben, propyl paraben, and butyl paraben).

Similar compositions employing other topically acceptable carrier compositions can be prepared according to standard pharmaceutical techniques. Other agents utilized in the treatment of acne can be incorporated, as can conventional pharmaceutical adjuvants such as fragrances, antioxidants, etc.

The nicotinate composition is applied to the loci of acne papules several times a day, typically 4 to 7 times a day; e.g., before and after meals and at bedtime, maximum activity being observed during the first twenty minutes following application. There appears to a favorable relationship between the frequency of application and observed response and since few if any side effects have been observed to date, the composition can be applied often with good results. Best results are obtained if the treatment is initiated at the onset of painful cystic lesions.

The compositions is applied to loci of acne papules. There is no advantage to applying such compositions to unaffected areas and the amount applied should be less than the amount which normally produces systemic effects.

The effectiveness of the treatment can be readily observed in the clinic. In one study, twenty subjects suffering from cystic acne presenting large (over 5 mm diameter) and tender papules applied to the loci of papules compositions containing 0.5% methyl nicotinate in a homogeneous cream carrier. Application was made repeated, typically four or more times per day. Such lesion when untreated generally persist in size and soreness for about three weeks. When treated with a nicotinate ester, the lesions often decreased in size and tenderness, in many cases after a few days, and associated pain was reduced.

TABLE

| Patient | Age/Sex | Diagnosis | Result |
| --- | --- | --- | --- |
| A | 46/F | Cystic Acne | Swelling of new |

TABLE-continued

| Patient | Age/Sex | Diagnosis | Result |
|---------|---------|-----------|--------|
| | | | lesions reduced in two days; older lesions responded in seven days on application q.i.d. |
| B | 27/M | Cystic Acne | Application b.i.d. No response |
| C | 31/F | Cystic Acne | Neck cyst suppressed on b.i.d. application; application increased to six times a day |
| D | 37/F | Cystic Acne | Lesions decreased on application t.i.d. |
| E | 34/F | Cystic Acne | Used on pilar cysts; No response |
| F | 28/F | Cystic Acne | Application t.i.d at onset stopped progression of lesion |
| G | 25/F | Cystic Acne | Hourly application at onset of chin cysts reduced lesion |
| H | 32/M | Cystic Acne | New lesions responded; older lesions did not |
| I | 24/F | Cystic Acne | Lesions responded in two to three days on application seven times a day |
| J | 23/M | Cystic Acne | New lesions partially cleared; patient complained of itch |
| K | 35/F | Cystic Acne | Constant eruption of new chin cysts controlled |
| L | 23/M | Cystic Acne | Lesions reduced on application t.i.d. over four to five days |
| M | 33/F | Cystic Acne | Lesions (sternum) reduced on application t.i.d. over ten days; brow lesions reduced in six days |
| N | 32/F | Cystic Acne | Application b.i.d. No response |
| O | 22/F | Cystic Acne | Lesions (back) reduced on application q.i.d. |
| P | 21/F | Cystic Acne | Four applications reduced pain |
| Q | 20/F | Cystic Acne | Lesions reduced 50% on application t.i.d. over three days |
| R | 26/M | Cystic Acne | Seven applications reduced lesion and pain over three days |
| S | 32/F | Cystic Acne | Seven applications per day reduced lesions and pain over three days; improvement noted in one day |
| T | 30/F | Cystic Acne | Application q.i.d. reduced pain and lesions; increased application rate to seven times a day |

What is claimed is:

1. The method of treating acne which comprises applying topically to the locus of an acne papule a composition in which the active ingredient consists essentially of a lower alkyl nicotinate of the formula:

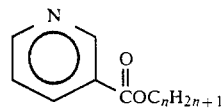

in which n has a value of from 1 to 6, said lower alkyl nicotinate being (i) present in an amount at least sufficient to treat acne but insufficient to effect systemic vasodilation and (ii) admixed with a topically acceptable and compatible pharmaceutical carrier.

2. The method of claim 1 wherein the lower alkyl nicotinate is methyl nicotinate.

3. The method of claim 2 wherein the methyl nicotinate is present in the carrier in a concentration of from about 0.5 to about 2% by weight of composition.

4. The method of claim 3 wherein the carrier comprises lanolin and petrolatum in a weight ratio of about 3:1.

5. The method of claim 4 wherein the concentration of the methyl nicotinate in the corner is from about 0.5 to about 1%.

* * * * *